United States Patent [19]

Goeldner et al.

[11] 3,996,042

[45] Dec. 7, 1976

[54] SYNERGISTIC HERBICIDAL COMPOSITIONS

[75] Inventors: Herbert Goeldner, Hallgarten; Robert Rudolf Schmidt, Cologne; Carl Metzger, Dormagen, all of Germany

[73] Assignee: Bayer Aktiengesellschaft, Leverkusen, Germany

[22] Filed: Jan. 31, 1975

[21] Appl. No.: 545,937

[30] Foreign Application Priority Data

Feb. 1, 1974 Germany ............... 2404979

[52] U.S. Cl. .................................................. 71/90
[51] Int. Cl.² ........................................... A01N 9/12
[58] Field of Search ........................................ 71/90

[56] References Cited
UNITED STATES PATENTS

| | | | |
|---|---|---|---|
| 3,682,614 | 8/1972 | Hack et al. | 71/90 |
| 3,726,892 | 4/1973 | Cebalo | 71/90 |
| 3,845,069 | 10/1974 | Schafer et al. | 71/90 |

*Primary Examiner*—Lewis Gotts
*Assistant Examiner*—Catherine L. Mills
*Attorney, Agent, or Firm*—Burgess, Dinklage & Sprung

[57] ABSTRACT

Synergistic herbicidal compositions are provided, containing as active ingredients: (1) 3-(benzthiazol-2-yl)-1,3-dimethyl-urea of the formula

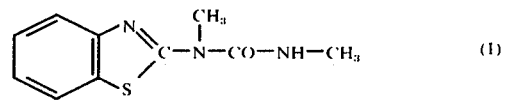

and (2) 3-(5-n-butylsulphonyl-1,3,4-thiadiazol-2-yl)-1,3-dimethyl-urea of the formula

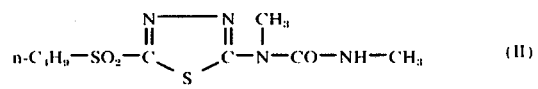

alone or in admixture with a solid or liquid or liquefied gaseous diluent or carrier.

8 Claims, No Drawings

SYNERGISTIC HERBICIDAL COMPOSITIONS

This invention relates to new herbicidal synergistic combinations of the herbicidally active compounds, 3-(benzthiazol-2-yl)-1,3-dimethyl-urea and 3-(5-n-butylsulphonyl-1,3,4-thiadiazol-2-yl)-1,3-dimethyl-urea.

It is known that 3-(benzthiazol-2-yl)-1,3-dimethyl-urea can be used as a selective herbicide in cereals from Belgian Patent 687,019. Furthermore, it is known that 3-(5-n-butylsulphonyl-1,3,4-thiadiazol-2-yl)-1,3-dimethyl-urea can be used as a herbicide, from German Offenlegungsschrift (German Published Specification) 1,816,568. However, the herbicidal activity of either preparation is not always satisfactory for combating weeds in cereals, especially in the case of weeds and wild grasses which are difficult to combat, if low amounts and low concentrations are used.

Thus, the action of 3-(benzthiazol-2-yl)-1,3-dimethyl-urea against cleavers (*Galium aparine*) is inadequate even if fairly high amounts are used. 3-(5-n-Butylsulphonyl-1,3,4-thiadiazol-2-yl)-1,3-dimethyl-urea is active against slender foxtail (*Alopecurus myosuroides*) only at high concentrations which lead to distinct damage to the crop plant.

The present invention provides a herbicidal composition containing as active ingredients (1) 3-(benzthiazol-2-yl)-1,3-dimethyl-urea of the formula

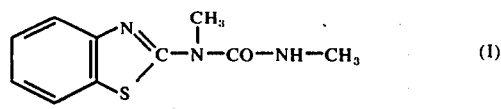

and (2) 3-(5-n-butylsulphonyl-1,3,4-thiadiazol-2-yl)-1,3-dimethylurea of the formula

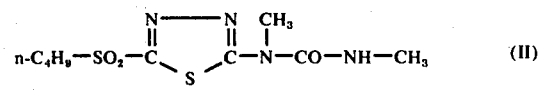

alone or in admixture with a solid or liquid or liquefied gaseous diluent or carrier.

The compositions of this invention display a particularly broad and selective herbicidal activity in cereal cultures.

The present invention also provides a method of combating weeds which comprises applying to the weeds or a weed habitat a composition of the present invention.

The present invention further provides means of yielding crops protected from damage by weeds by being grown in areas in which immediately prior to and/or during the time of the growing a composition of the present invention was applied. It will be seen that the usual methods of providing a harvested crop may be improved by the present invention.

Surprisingly, the activity of the composition according to the present invention is substantially greater than the sum of the actions of the individual active compounds. An unforeseeable genuine synergistic effect is involved, and not just a complementary action. This synergistic effect manifests itself particularly markedly at certain concentration ratios.

The active-compound combination according to the invention offers the advantage, compared to the individual active compounds known from the state of the art, that the weeds or wild grasses *Galium aparine* and *Alopecurus myosuroides* which are otherwise very difficult to combat can be combated reliably by the compositions according to the invention. Examples of such weeds are species of *Chenopodium, Stellaria, Veronica, Lamium, Papaver* and *Capsella*. If higher amounts are used, the active compound combination according to the invention is also suitable for the total combating of weeds.

The active compounds (I) and (II) and their preparation are already known; see U.S. Pat. No. 1,756,135 for compound (I) and German Offenlegungsschrift (German Published Specification) 1,816,568 for compound (II). A particularly suitable method of preparation for active compound (II) is given in the Examples herein.

The weight ratio of the active compounds (I) and (II) in the active compound combination can be varied within a relatively large range. In general, 0.1 to 5 parts by weight of active compound (II), preferably 0.2 to 2 parts by weight, are used per part by weight of active compound (I).

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaeous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

Other active compounds can be present, together with the active compound combination according to the invention, in the formulations. The formulations in general contain from 0.1 to 95 percent by weight of active compound, preferably from 0.5 to 90 percent by weight.

The active-compound combination can be used as such, in the form of its formulations or in the use forms prepared therefrom, such as ready-to-use solutions, emulsions, suspensions, powders, pastes and granules. They may be used in the customary manner, for example by dusting, atomizing, spraying, watering and scattering.

The amounts used of the active-compound combination according to the invention can be varied within a fairly wide range. In general, the amounts used are from 0.1 to 10 kg/ha, preferably from 0.1 to 5 kg/ha.

The active-compound combination according to the invention is normally used before the emergence of the plants, although it can also be used after the emergence of the plants.

While the individual active compounds show weaknesses in herbicidal action, the combination shows a very broad action against weeds, which goes beyond a simple summation of the actions.

A synergistic effect is considered to exist in herbicides whenever the herbicidal action of the active compound combination is greater than that of the individually applied active compounds.

The action to be expected for a given combination of two herbicides can be calculated as follows (see COLBY, S.R., "Calculating synergistic and antagonostic response of herbicide combinations," Weeds 15, pages 20–22, 1967). If X = % damage by Herbicide A when using p kg/ha and Y = % damage by Herbicide B when using q kg/ha and E = the expected damage by Herbicides A and B when using p + q kg/ha, then E = X + Y − X.Y/100.

If the actual damage is greater than calculated, the action of the combination is super-additive, that is to say a synergistic effect exists.

The good herbicidal action of the active compound combination can be seen from the Examples which follow. The tables of Examples A and B show clearly that the found herbicidal action of the active compound combination according to the invention against weeds is greater than the calculated action, that is to say a genuine synergistic effect exists.

EXAMPLE A

Example A

Post-emergence test
Solvent:    5 parts by weight of acetone

Example A-continued

Post-emergence test
Emulsifier:    1 part by weight of alkylaryl polyglycol ether To produce a suitable preparation of the active compound(s) was mixed with the stated amount of solvent; the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. Depending on the concentration of the spray liquor, the amount of water used was between 1,000 and 2,000 l/ha. After three weeks, the degree of damage to the plants was determined in % damage in comparison to the development of the untreated control. The figures denote:

0% = no action

100% = total destruction

The active compounds, the amounts used and the results can be seen from the table which follows:

Table A

Post-emergence test/greenhouse
Percentage damage to weeds and wild grasses in cereal cultures

| Active compound | Amount of active compound used, kg/ha | Chenopodium album found | calc. | Galium aparine found | calc. | Alopecurus myosuroides found | calc. | Barley | Wheat |
|---|---|---|---|---|---|---|---|---|---|
| (I) | 0.2 | 70 | | 0 | | 0 | | 0 | 0 |
| (known) | 0.4 | 90 | | 20 | | 20 | | 0 | 0 |
| | 0.6 | 100 | | 40 | | 50 | | 0 | 0 |
| (II) | 0.1 | 100 | | 0 | | 0 | | 0 | 0 |
| (known) | 0.2 | 100 | | 40 | | 20 | | 0 | 0 |
| | 0.4 | 100 | | 70 | | 40 | | 0 | 0 |
| Combination | (I) + (II) | | | | | | | | |
| (I) + (II) | 0.2 + 0.2 | 100 | 100 | 60 | 40 | 60 | 20 | 0 | 0 |
| according to | 0.2 + 0.1 | 100 | 100 | 60 | 0 | 60 | 0 | 0 | 0 |
| the invention | 0.4 + 0.1 | 100 | 100 | 60 | 20 | 50 | 20 | 0 | 0 |
| | 0.6 + 0.1 | 100 | 100 | 90 | 40 | 60 | 50 | 0 | 0 | found = damage found
calc. = damage calculated from the Colby formula given earlier.

EXAMPLE B FIELD EXPERIMENTS

Example B field experiments
(a) Pre-emergence test/test in the open
Solvent:    5 parts by weight of acetone
Emulsifier:    1 part by weight alkylaryl polyglycol ether To produce a suitable preparation of the active compound(s), 1 part by weight of the active compound(s) was mixed with the stated amount of solvent; the stated amount of emulsifier was added and the concentrate was diluted with water to the desired concentration.

Shortly after sowing the test plants in the open, the individual plots were watered with the amount of the active-compound preparation required for uniform wetting of the soil surface. The active compound concentration in the preparation was immaterial, and only the amount of active compound used per unit area was decisive.

After 5 weeks, the degree of damage of the test plants was rated in % damage in comparison to the development of the untreated control. The figures denote:

0% = no action

100% = total destruction

The active compounds, the amounts used and the results can be seen from Table B which follows:

| (b) Post-emergence test/test in the open | |
|---|---|
| Solvent: | 5 parts by weight of acetone |
| Emulsifier: | 1 part by weight of alkylaryl polyglycol ether |

To produce a suitable preparation of the active compound(s), 1 part by weight of the active compound(s) was mixed with the stated amount of solvent; the stated amount of emulsifier was added and the concentrate was diluted with water to the desired concentration.

In the open, plots of test plants, which were about 3–10 cm high, were sprayed with an amount of the active-compound preparation such as to give uniform wetting of the plants. The decisive factor was the amount of active compound used per unit area. After three weeks, the degree of damage of the plants was rated in % damage in comparison to the untreated control. The figures denote:

0% = untreated control/no action
100% = total destruction

The active compounds, the amounts used and the results can be seen from Table B which follows.

EXAMPLE C

The experiment was carried out in the same manner as described in Example B in order to evaluate the damage to weeds in cereal cultures when the active-compound preparations are applied by the pre-emergence or post-emergence methods.

The active compounds, the amounts used and the results can be seen from Table C which follows.

100 ml of ethyl acetate. After the heat of reaction had subsided, the mixture was heated for a further 4 hours under reflux. The solvent was then distilled off; the 3-(5-n-butylsulphonyl-1,3,4-thiadiazol-2-yl)-1,3-dimethyl-urea (II) which remained as the crude product was recrystallized from petroleum ether/acetone. Melting point 129° C.

b. Preparation of 2-n-butylsulphonyl-5-methylamino-1,3,4-thiadiazole: 77 ml (1.1 mole) of 50% strength hydrogen peroxide were added dropwise over the course of 30 minutes to a solution of 50.8 g (0.25 mole) of 2-n-butylmercapto-5-methylamino-1,3,4-thiadiazole in 65 ml of 20% strength sulphuric acid at 30°–50° C. The reaction mixture was kept at 60° C for 4 hours. After cooling, the solution was neutralized with concentrated ammonia solution. The 2-n-butylsulphonyl-5-methylamino-1,3,4-thiadiazole which crystallized from ethyl acetate; yield 52.8 g (90% of theory). Melting point 107°–108° C.

c. Preparation of 2-n-butylmercapto-5-methylamino-1,3,4-thiadiazole: 27.4 g (0.2 mole) of n-butyl bromide were added dropwise over the course of 20 minutes to a solution of 29.4 g (0.2 mole) of 2-mercapto-5-methylamino-1,3,4-thiadiazole and 13.4 g (0.24 mole) of potassium hydroxide in 120 ml of dimethylsulphoxide at 10°–20° C. The reaction mixture was kept at 50° C for 2 hours. After cooling, the mixture was poured into 600 ml of water. The product which had separated out was filtered off, dried and recrystallized from ligroin. Yield 93% of theory; melting point 67°–68° C.

d. Preparation of 2-mercapto-5-methylamino-1,3,4-thiadiazole: 420 ml (7 moles) of carbon disulphide were added dropwise to a suspension of 400 g (3.82 moles) of 4-methylthiosemi-carbazide in 2,000 ml of

Table B

Pre-emergence and post-emergence test/in the open
Percentage damage to weeds and wild grasses in field experiments

| | | (a) pre-emergence | | | | (b) post-emergence | | | | |
|---|---|---|---|---|---|---|---|---|---|---|
| | Amount of active compound used, | Galium aparine | | Alopecurus myosuroides | | Galium aparine | | Alopecurus myosuroides | | |
| Active compound | kg/ha | found | calc. | found | calc. | Wheat | found | calc. | found | calc. | Wheat |
| (I) | 0.7 | 0 | | 32 | | 0 | 0 | | 32 | | 0 |
| (known) | 1.4 | 0 | | 65 | | 0 | 0 | | 65 | | 0 |
| (II) | 0.7 | 32 | | 10 | | 0 | 65 | | 10 | | 0 |
| (known) | 1.4 | 65 | | 85 | | 0 | 90 | | 85 | | 0 |
| (I) + (II) | 0.7 + 1.4 | 75 | 32 | 95 | 89.8 | 0 | 90 | 90 | 85 | 89.8 | 0 |
| | 1.4 + 1.4 | 100 | 65 | 100 | 94.75 | 0 | 100 | 90 | 100 | 94.75 | 0 |
| | 1.4 + 0.7 | 90 | 32 | 100 | 68.5 | 0 | 95 | 65 | 95 | 68.5 | 0 |

Table C

Percentage damage to weeds in cereal culture/field experiments (a) pre-emergence

| Active compound combination | Amount of active compound used, kg/ha | Stellaria media | Veronica hederifolia | Lamium amplexicaule | Capsella bursa p. | Winter barley |
|---|---|---|---|---|---|---|
| (I) + (II) | 1.4 + 1.4 | 100 | 97 | 100 | 100 | 0 | b) post-emergence

| Active compound combination | Amount of active compound used, kg/ha | Stellaria media | Veronica hederifolia | Papaver rhoeas | Viola tricolor | Winter rye |
|---|---|---|---|---|---|---|
| (I) + (II) | 1.4 + 1.4 | 100 | 100 | 100 | 95 | 0 |

The preparation of active compound (II) may be effected as follows:

a. 7.2 g (0.126 mole) of methyl isocyanate were added dropwise to a solution of 29.5 g (0.126 mole) of 2-n-butylsulphonyl-5-methylamino-1,3,4-thiadiazole in dimethylformamide at 30° C. The reaction mixture was kept at 80°–90° C for 3 hours and was then cooled and poured into 4,000 ml of water. The product which hereupon crystallized out was filtered off, washed and dried. Yield: 505 g (= 90% of theory); melting point 181°–183° C.

It will be understood that the specification and examples are illustrative but not limitative of the present invention and that other embodiments within the spirit and scope of the invention will suggest themselves to those skilled in the art.

What is claimed is:

1. Herbicidal composition containing, in herbicidally effective amounts, as active ingredients
   1. 3-(benzthiazol-2-yl)-1,3-dimethyl-urea of the formula

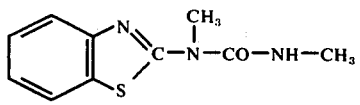

and 2. 3-(5-n-butylsulphonyl-1,3,4-thiadiazol-2-yl)-1,3-dimethyl-urea of the formula

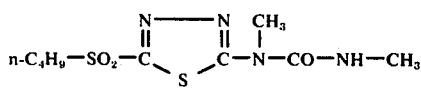

in a ratio of compound (I) to compound (II) of 1:0.5 to 1:1.

2. Composition as claimed in claim 1, in which the weight ratio of compound (I) to compound (II) is about 1:0.5.

3. Composition as claimed in claim 1, in which the weight ratio of compound (I) to compound (II) is about 1:1.

4. Composition as claimed in claim 1, containing from 0.1 to 95% of total active compounds, by weight.

5. Method of combating weeds, which method comprises applying to the weeds or their habitat a herbicidal composition containing, in herbicidally effective amounts, as active ingredients
   1. 3-(benzthiazol-2-yl)-1,3-dimethyl-urea of the formula

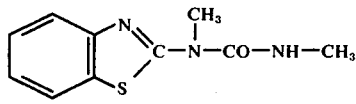

and 2. 3-(5-n-butylsulphonyl-1,3,4-thiadiazol-2-yl)-1,3-dimethyl-urea of the formula

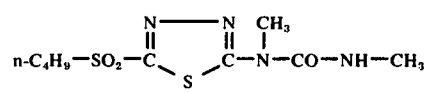

in a ratio of compound (I) to compound (II) of 1:0.5 to 1:1.

6. Method as claimed in claim 5, wherein the active ingredients are applied to an area of agriculture in an amount of 0.1 to 10 kg of total active ingredients per hectare.

7. Method as claimed in claim 6, wherein the active ingredients are applied to an area of agriculture in an amount of 0.1 to 5.0 kg of total active ingredients per hectare.

8. Composition as claimed in claim 1, also comprising, in admixture with the active ingredients, a solid or liquid or liquefied gaseous carrier.

* * * * *